United States Patent [19]
Gumbrecht et al.

[11] Patent Number: 5,900,128
[45] Date of Patent: May 4, 1999

[54] ELECTROCHEMICAL SENSOR

[75] Inventors: Walter Gumbrecht, Herzogenaurach; Bernhard Montag, Forchheim; Reinhard Kress, Erlangen, all of Germany

[73] Assignee: Siemens Aktiengesellschaft, Munich, Germany

[21] Appl. No.: 08/866,103

[22] Filed: May 30, 1997

[30] Foreign Application Priority Data

May 31, 1996 [DE] Germany ............................ 196 21 997

[51] Int. Cl.⁶ .................................................. G01N 27/404
[52] U.S. Cl. .......................... 204/415; 204/414; 204/426; 205/783; 205/784
[58] Field of Search ........................... 204/415, 421–429; 205/782.5, 783, 783.5, 784

[56] References Cited

U.S. PATENT DOCUMENTS

| | | | |
|---|---|---|---|
| 4,961,833 | 10/1990 | Sakai et al. | 204/415 |
| 5,035,791 | 7/1991 | Battilotti et al. | 204/415 |
| 5,200,051 | 4/1993 | Cozzette et al. | 204/415 |
| 5,284,140 | 2/1994 | Allen et al. | 204/415 |
| 5,376,255 | 12/1994 | Gumbrecht et al. | 204/415 |
| 5,393,399 | 2/1995 | Van Den Berg et al. | 204/415 |
| 5,431,806 | 7/1995 | Suzuki et al. | 204/415 |
| 5,510,013 | 4/1996 | Hippe et al. | 204/415 |
| 5,518,601 | 5/1996 | Foos et al. | 204/415 |

FOREIGN PATENT DOCUMENTS

| | | |
|---|---|---|
| 0 100 667 A1 | 7/1982 | European Pat. Off. . |
| WO 91/11710 | 1/1991 | WIPO . |

OTHER PUBLICATIONS

Article entitled: "An Integrated Chemical Sensor with Multiple Ion and Gas Sensors", Tsukada et al., *Sensors and Actuators B*, vol. 2, (1990) month unavailable, pp. 291–295.

Primary Examiner—T. Tung
Attorney, Agent, or Firm—Hill & Simpson

[57] ABSTRACT

An electrochemical sensor is provided on a substrate whereby a precious metal layer is arranged in an inner region under an electrolyte layer that is surrounded by a polyimide structure. A hydrophobic layer is surrounded by an outer polyimide structure and further is located on top of the electrolyte layer and extends laterally beyond the electrolyte layer. A lead for electrical connection of the precious metal layer extends under the hydrophobic layer laterally from the electrolyte layer is sealed from the hydrophobic layer by a protective layer. The protective layer prevents the penetration of analysis fluid into the gap between the hydrophobic layer and the surrounding polyimide structure into the inner region of the sensor. The material of the protective layer is preferably a double layer of PECVD oxide and PECVD nitride.

20 Claims, 2 Drawing Sheets

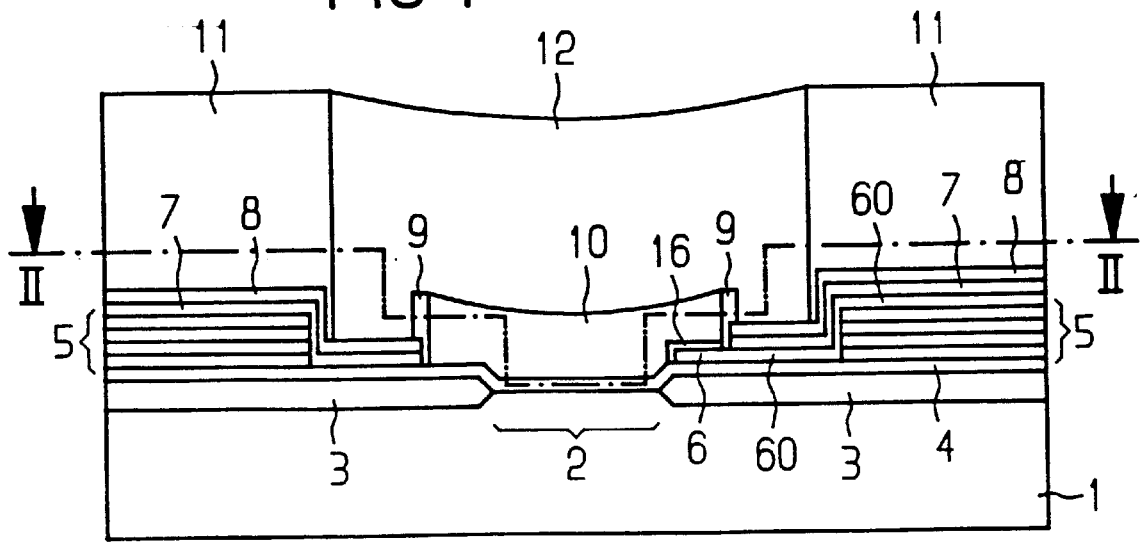
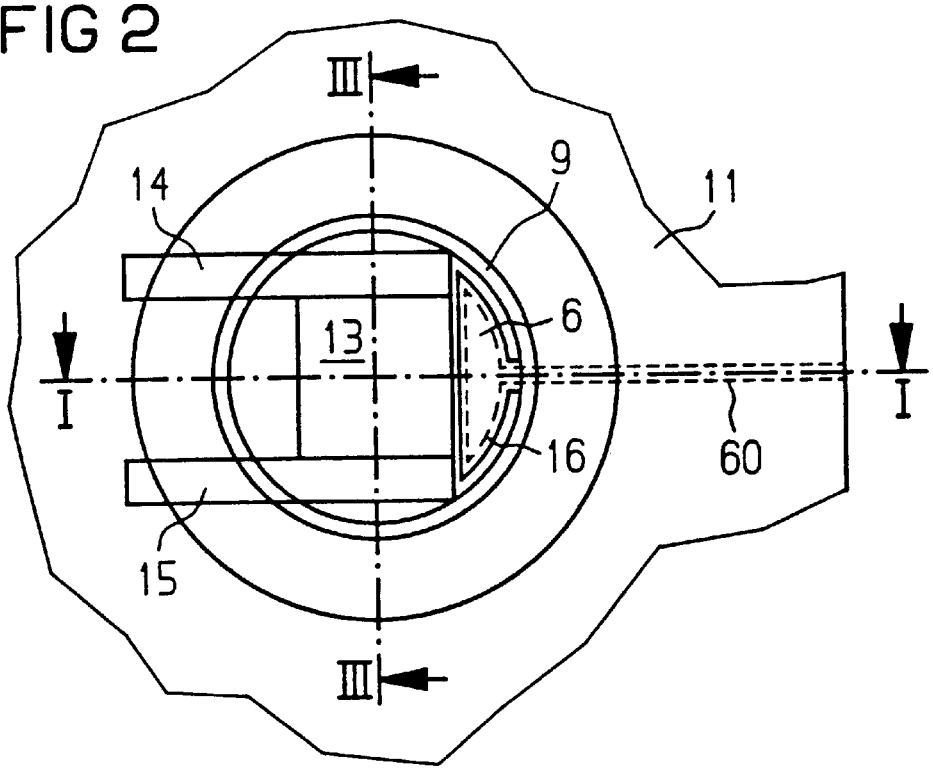

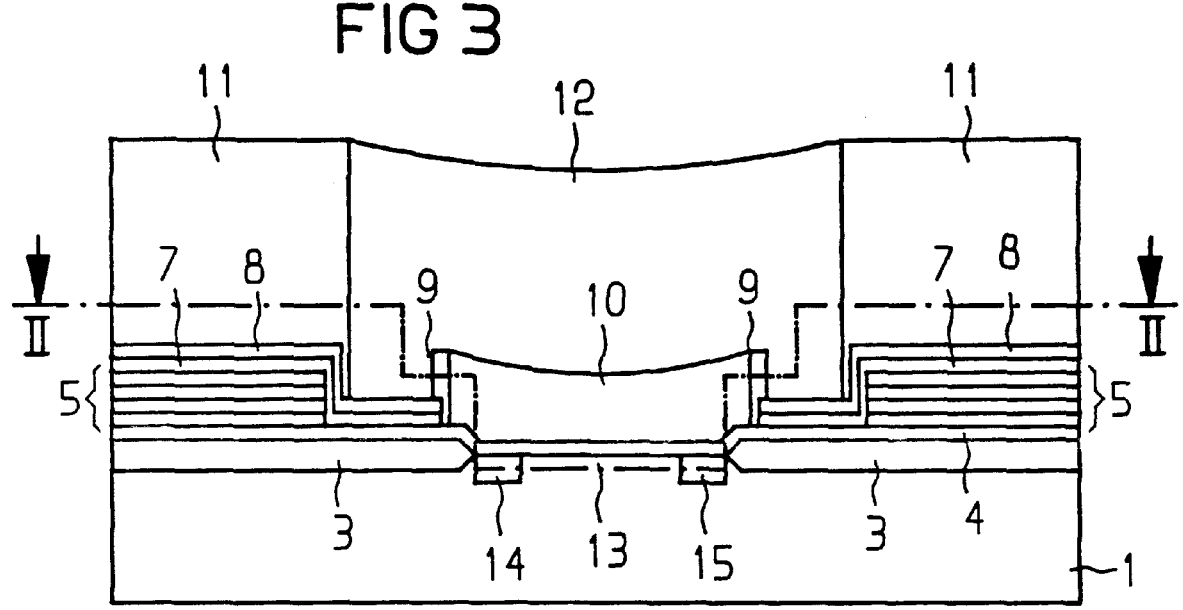

ELECTROCHEMICAL SENSOR

BACKGROUND OF THE INVENTION

The present invention is directed to an electrochemical sensor that can be employed for the determination of the concentrations of gases such as, $O_2$ or $CO_2$.

U.S. Pat. No. 5,376,255 discloses a gas sensor wherein an electrochemical sensor is fashioned on a planar substrate of semiconductor material such as silicon. This sensor comprises a pH-sensitive electrode such as $IrO_2$, or a pH-sensitive ISFET (ion-selective field effect transistor). Independently of the sensor, which is matched to the gas ($O_2$, $CO_2$) to be defined, a reference electrode preferably composed of a precious metal is present in such a sensor. For example, this precious metal is platinum. In potentiometric sensors, however, silver, silver chloride electrodes are present.

The sensor and reference electrode are covered with an electrolyte layer. This electrolyte layer is surrounded on all sides by an annular structure of polyimide or some other polymer such as, for example, polybenzoxazole. A hydrophobic layer is applied over the electrolyte layer and laterally relative thereto. The hydrophobic layer being in turn surrounded by a second or outer polymer structure. The outer annular polymer structure is higher than the inner polymer structure that encloses the electrolyte layer.

The problem arises with this arrangement is that there is an inadequate adhesion between the hydrophobic layer, which is usually polysiloxane, and the polyimide structure. A crack is therefore formed between the hydrophobic layer and the framing. Due to the slight thickness of the hydrophobic layer, approximately 20 μm through 30 μm, this crack formation results therein that an analysis fluid (electrolyte solution or blood) to be examined can enter the crack and short-circuits the electrode of precious metal with a cooperating electrode of the sensor or electrically conductive regions of the sensor base structure. The fluid penetration can also result in corrosion of one or both of the electrodes.

Therefore, there is a need for an improved electrochemical sensor with a structure that is not prone to cracking or to fluid leakage which can result in a short circuiting or corrosion of the sensor.

SUMMARY OF THE INVENTION

It is an object of the present invention to specify an electrochemical sensor as semiconductor component that is constructed in the initially described arrangement but wherein the described problem does not occur.

The electrochemical sensor of the present invention comprises at least one electrode disposed on top of a substrate. In an embodiment, the electrode is fabricated from a precious metal. An electrolyte layer is disposed on top of at least a portion of the electrode. The electrolyte layer is surrounded by a first polymer structure. The first polymer structure surrounds an electrochemically sensitive region of the substrate. A hydrophobic layer is disposed on top of the electrolyte layer and extends laterally beyond the first polymer structure and the electrolyte layer. The hydrophobic layer is surrounded by a second polymer structure. A further or connecting portion of the electrode extends laterally beyond the electrolyte layer and between the substrate and hydrophobic layer. A protective layer is disposed between the further portion of the electrode and the hydrophobic layer which prevents the penetration of analysis fluid into the gap between the hydrophobic layer and the first polymer structure.

In an embodiment, the hydrophobic layer comprises a material that exhibits a high diffusion coefficient for at least one specific gas.

In an embodiment, the protective layer comprises a material that enters into a covalent bond with the material of the hydrophobic layer.

In an embodiment, the hydrophobic layer comprises a polysiloxane and the protective layer comprises oxygen.

In an embodiment, the protective layer comprises an oxide layer. The oxide layer may be silicon oxide or $SiO_xN_y$.

In an embodiment, an oxide layer is formed on top of the silicon nitride layer of the protective layer.

In an embodiment, the protective layer comprises a double layer with a lower oxide layer and an upper nitride layer. In a further embodiment, an oxide layer is formed on top of the upper nitride layer.

In an embodiment, the nitride layer of the protective layer is a PECVD nitride layer.

In an embodiment, the oxide layer of the protective layer is a PECVD oxide layer.

The inventive sensor solves the problem in that a protective layer that is preferably a double layer of a PECVD oxide and of a PECVD nitride is applied between the precious metal electrode of the sensor and the hydrophobic layer that terminates the sensor toward the top. Dependent on the material employed for the hydrophobic layer, the protective layer can be selected from correspondingly matched materials. A material with high diffusion coefficient for the gas to be defined is required as material for the hydrophobic layer for the function of the sensor.

In order to offer an adequate protective effect for the precious metal electrode arranged therebelow, the material of the protective layer is selected such that it enters into an intimate union with the hydrophobic layer, by contrast to the polymer of the surrounding polymer structure. A material is preferably employed that enters into a covalent bond with the hydrophobic layer. Given employment of polysiloxane for the hydrophobic layer, various oxides preferably come into consideration for the protective layer. Given employment of a nitride layer such as deposited during the course of manufacturing semiconductor components, for example as in PECVD nitride (plasma enhanced chemical vapor deposition), a thin oxidized layer forms at the surface of this layer. In the case of a silicon nitride layer ($Si_3N_4$), this thin oxide layer is $SiO_xN_y$. Silicon nitride, which is particularly suited for the passivation, is therefore also suitable for entering into a covalent and, thus, intimate bond with the material of the hydrophobic layer and thus offering a sealing of the hydrophobic layer relative to the precious metal electrode.

BRIEF DESCRIPTION OF THE DRAWINGS

FIG. 1 is a cross sectional view of an embodiment of the sensor of the present invention taken substantially along line I—I of FIG. 2.

FIG. 2 is a cross sectional view taken substantially along line II—II of FIG. 1 but which illustrates an alternative embodiment.

FIG. 3 is a cross sectional view taken substantially along line III—III of FIG. 2.

It should be understood that the drawings are not necessarily to scale and that the embodiments are sometimes illustrated by phantom lines, diagrammatic representations and fragmentary views. In certain instances, details which are not necessary for an understanding of the present inven-

DETAILED DESCRIPTION OF THE PRESENTLY PREFERRED EMBODIMENTS

Given the arrangement of FIG. 1, a basic structure of the sensor, which is formed by a structure of ISFET provided in the region 2 in the illustrated, simple example, is located on a substrate 1 that, for example, can be silicon or the like. This region 2 is electrically insulated on=, sides, this occurring with insulating regions 3 in this example. These insulating regions 3 can be produced on a silicon substrate, for example by a thermal oxidation (LOCOS). In an alternative embodiment of the sensor, this insulator region 3 can also be present surface-wide in the region of the sensor in order to effectively insulate the electrical terminals of the sensor from the substrate 1. In the example illustrated in FIG. 1, a sensor layer 4 is located surface-wide over said regions. This sensor layer 4, as illustrated, is applied surface-wide or is at least present in a region projecting somewhat beyond the region 2. This sensor layer 4 can be an electrical insulation layer for insulation from the material of the substrate 1. For example, an oxide layer (silicon oxide) or a nitride layer ($Si_3N_4$) can serve as such an insulator layer as employed, for example, in an amperometric sensor. In the described, somewhat more complicated example of a potentiometric sensor that comprises an ISFET, this sensor layer 4 is composed at least of an oxide layer forming the gate oxide of the ISFET and of a nitride layer that functions as pH-sensitive layer and is deposited thereon preferably with LPCVD (low pressure chemical vapor deposition).

The electrode of precious metal, preferably, for example platinum, is applied on this basic structure. In the exemplary embodiment shown in FIG. 1, further layers 5 are arranged at this side, these, for example, being composed of various dielectrics and being provided, for example, for the integration of further components or various metalizations or interconnect levels of wirings. The layer of precious metal that forms the actual precious metal layer 6 in the region of the sensor is then applied such that a lateral portion forming an electrical lead 60 is located on the surface of the lateral layers 5. This lateral lead 60 can also be present between the lateral layers as one of the various interconnect levels provided between the dielectric layers. The electrically conductive lead 60 of the precious metal that has been provided is interpreted here and in the claims as being a component part of the precious metal layer 6. In the case of the potentiometric sensor with ISFET described in FIG. 3, a further layer 16 that forms an Ag/AgCl electrode is provided and is connected to layer the precious metal layer 6 of platinum which serves as a supply line. This embodiment is particularly useful for measuring the concentration of $CO_2$. This electrode is produced, for example, in that a thin layer of silver is deposited on the platinum layer 6 and this silver is subsequently chemically or electrochemically chlorinated. The inventively provided protective layer is formed by a double layer in this example that is composed of a PECVD oxide layer 7 and of a PECVD nitride layer 8. The oxide is preferably silicon oxide ($SiO_2$); the nitride layer is preferably silicon nitride ($Si_3N_4$). Instead, a simple layer of an oxide, preferably silicon oxide, can be present as protective layer. TEOS (tetraethylorthosilicate) particularly comes into consideration for this oxide. An oxide forms at the surface of a $Si_3N_4$ layer when this nitride layer is exposed to the influence of oxygen. The nitride layer 8 in this example therefore has a thin oxide layer of $SiO_xN_y$ at the upper side. It is therefore suitable for entering - via the oxygen - into a covalent bond with polysiloxane that is employed for the hydrophobic membrane 12.

An electrolyte layer 10 is located on the base region 2 of the sensor within an inner polymer structure 9 (for example, polyimide). Some other polymer such as, for example, polybenzoxazol, can be employed for the embracing structure 9 instead of polyimide. A hydrophobic layer 12 embraced by an outer polymer structure 11 (for example, of polyimide) is located over this electrolyte layer 10 and laterally thereto. When the layers 5 annularly surrounding the sensor are omitted, the protective layer 7, 8 is applied in an annularly and planar manner. A step derives only in the region of the precious metal layer 6 and its lead 60.

In order to illustrate this arrangement, the section indicated dot-dashed in FIG. 1 is shown in FIG. 2. The outer region occupied by the outer polymer structure 11, the inner semiconductor region forming the gate region 13 of the ISFET present in this example, regions of source 14 and drain 15 arranged laterally thereto, the inner polymer structure 9 and the platinum layer 6 with the lead 60 can be seen in FIG. 2. The Ag/AgCl electrode 16 is applied on and adjacent to the part of the platinum layer 6 projecting into the inside of the inner polymer structure 9. The lead 60 for the electrical connection of the layer 6 is located - as a narrow strip - either in the layer plane of the layer 6 or is brought to these layers in a step given the presence of the dielectric layers 5. The protective layer 7, 8 is located behind the plane of the drawing in the region outside the annularly entered, inner polymer structure 9. The protective layer 7, 8 forms steps at the edges of the lead 60 to the layer 6.

FIG. 3 shows the further cross section entered in FIG. 2. In addition to the component parts that are entered in FIG. 1, the gate region 13, the source region 14 and the drain region 15 in a region of the basic structure of ISFET are found in FIG. 3. The regions of source and drain are lengthened outward for the electrical connection behind the plane of the drawing; the precious metal layer 6 with the lead 60 is located in front of the plane of the drawing.

The inventive sensor can be realized on the basis ot a fundamentally arbitrary structure. The arrangement with precious metal electrode, protective layer located thereon and hydrophobic membrane arranged there over can be realized in potentiometric, and amperometric and conductometric sensors. In the alternative embodiments, the corresponding means are then provided, or respectively omitted compared to the exemplary embodiment described with reference to the Figures. The doped regions 13, 14, 15 formed in the substrate of semiconductor material are omitted given an amperomatric sensor. In such a sensor, an arrangement of at least two, preferably three electrodes is located on an insulation layer that, for example, can be composed of a surface-wide, insulating layer of silicon produced with LOCOS. These electrodes, which include at least one precious metal electrode corresponding to the electrode 6 of the illustrated exemplary embodiment, are arranged in the upper side of an insulating layer in the inner region of the sensor under the electrolyte layer 10. The protective layer 7, 8, corresponding to the arrangement of the described exemplary embodiment, is present at least in the region of the lead to a precious metal electrode between this precious metal and the hydrophobic layer. However, the protective layer preferably interrupts the entire annular region around the inner polymer structure 9 and seals the hydrophobic layer 12 from the outside. The conductometric sensor differs therefrom in that two electrodes are arranged in the sensor region at a relatively small distance from one another in order to measure the conductivity of the material of the electrolyte layer present there between. This conductivity changes as a consequence of the admitted gases.

From the above description, it is apparent that the objects and advantages of the present invention have been achieved. While only certain embodiments have been set forth, alternative embodiments and various modifications will be apparent from the above description to those skilled in the art. These and other alternatives are considered equivalents and within the spirit and scope of the present invention.

We claim:

1. An electrochemical sensor comprising:
    at least one electrode fabricated from a precious metal disposed on top of a substrate,
    an electrolyte layer being disposed on top of at least a portion of the electrode, the electrolyte layer being surrounded by a first polymer structure,
    the first polymer structure further surrounding an electrochemically sensitive region of the substrate,
    a hydrophobic layer being disposed on top of the electrolyte layer and the first polymer structure and extending laterally beyond the first polymer structure and the electrolyte layer, the hydrophobic layer being surrounded by a second polymer structure and engaged by the second polymer structure at an outer periphery of the hydrophobic layer,
    a further portion of the electrode extending laterally beyond the electrolyte layer and the first polymer structure and between the substrate and the hydrophobic layer and further between the second polymer structure and the substrate,
    a protective layer being disposed between the further portion of the electrode and the hydrophobic layer, between the further portion of the electrode and the second polymer structure, and between the further portion of the electrode and the periphery of the hydrophobic layer where the second polymer structure engages the hydrophobic layer.

2. The sensor of claim 1 wherein the hydrophobic layer comprises a material that exhibits a high diffusion coefficient for at least one specific gas.

3. The sensor of claim 2 wherein the protective layer comprises a material that enters into a covalent bond with the material of the hydrophobic layer.

4. The sensor of claim 3 wherein the hydrophobic layer comprises a polysiloxane and wherein the protective layer comprises oxygen.

5. The sensor of claim 4 wherein the protective layer comprises an oxide layer.

6. The sensor of claim 5 wherein the oxide layer is a silicon oxide.

7. The sensor of claim 5 wherein the oxide layer is $SiO_xN_y$.

8. The sensor of claim 5 wherein the protective layer further comprises the oxide layer disposed on top of a silicon nitride layer.

9. The sensor of claim 3 wherein the protective layer comprises a double layer comprising a lower oxide layer and an upper nitride layer, the oxide layer being disposed on top of the electrode and the nitride layer being disposed between the oxide layer and the hydrophobic layer.

10. The sensor of claim 9 wherein an upper oxide layer is formed on the surface of the upper nitride layer.

11. The sensor of claim 9 wherein the oxide is a PECVD oxide layer.

12. The sensor of claim 9 wherein the nitride layer is a PECVD nitride layer.

13. An electrochemical sensor comprising:
    at least one electrode disposed on top of a substrate, at least a first portion of the electrode being disposed between the substrate and an electrolyte layer,
    the electrolyte layer being surrounded by a first polymer structure, the electrolyte layer and first polymer structure being disposed underneath a hydrophobic layer that extends laterally beyond the first polymer structure and the electrolyte layer,
    the hydrophobic layer being surrounded by a second polymer structure and engaged by the second polymer structure at an outer periphery of the hydrophobic layer,
    a second portion of the electrode extending laterally beyond the electrolyte layer and between the substrate and the hydrophobic layer and further between the second polymer structure and the substrate,
    the second portion of the electrode being disposed underneath a protective layer,
    the protective layer being disposed between the second portion of the electrode and the hydrophobic layer between the second portion of the electrode and the second polymer structure and between the second portion of the electrode and the periphery of the hydrophobic layer where the second polymer engages the hydrophobic layer.

14. The sensor of claim 13 wherein the first polymer structure surrounds an electrochemically sensitive region of the substrate.

15. The sensor of claim 13 wherein the electrode is fabricated from a precious metal.

16. The sensor of claim 13 wherein the hydrophobic layer comprises a material that exhibits a high diffusion coefficient for at least one specific gas and wherein the protective layer comprises a material that enters into a covalent bond with the material of the hydrophobic layer.

17. The sensor of claim 16 wherein the protective layer comprises a double layer comprising a lower oxide layer and an upper nitride layer, the oxide layer being disposed on top of the electrode and the nitride layer being disposed between the oxide layer and the hydrophobic layer.

18. The sensor of claim 17 wherein the oxide layer is a PECVD oxide layer and wherein the nitride layer is a PECVD nitride layer. protective layer comprises a material that enters into a covalent bond with the material of the hydrophobic layer.

19. The sensor of claim 13 wherein the hydrophobic layer comprises a polysiloxane and wherein the protective layer comprises an oxide layer.

20. An electrochemical sensor comprising:
    at least one electrode fabricated from a precious metal disposed on top of a substrate,
    an electrolyte layer being disposed on top of at least a portion of the electrode, the electrolyte layer being surrounded by a first polymer structure,
    the first polymer structure further surrounding an electrochemically sensitive region of the substrate,
    a hydrophobic layer being disposed on top of the electrolyte layer and the first polymer structure and extending laterally beyond the first polymer structure and the electrolyte layer, the hydrophobic layer being surrounded by a second polymer structure and engaged by the second polymer structure at an outer periphery of the hydrophobic layer, the hydrophobic layer comprising a material that exhibits a high diffusion coefficient for at least one specific gas, the hydrophobic layer comprising polysiloxane, a further portion of the electrode extending laterally beyond the electrolyte layer and between the substrate and the hydrophobic layer and further between the second polymer structure and the substrate, a protective layer being disposed between the further portion of the electrode and the hydrophobic layer between the further portion of the electrode and the second polymer structure, and between the further portion of the electrode and the periphery of the hydrophobic layer where the second polymer structure engages the hydrophobic layer, the protective layer comprising a double layer comprising a lower oxide layer and an upper nitride layer, the oxide layer being disposed on top of the further portion of the electrode and the nitride layer being disposed between the oxide layer and the hydrophobic layer and between the oxide layer and the second polymer structure and between the oxide layer and an area where the second polymer structure engages the hydrophobic layer, the nitride layer entering into a covalent bond with the material of the hydrophobic layer.

* * * * *